US00PP17313P2

(12) United States Plant Patent
Hansen

(10) Patent No.: US PP17,313 P2
(45) Date of Patent: Dec. 26, 2006

(54) ***HOSTA* PLANT NAMED 'HIGH SOCIETY'**

(50) Latin Name: *Hosta hybrida*
Varietal Denomination: High Society

(75) Inventor: Hans Andrew Hansen, Waseca, MN (US)

(73) Assignee: Shady Oaks Nursery, LLC, Waseca, MN (US)

( * ) Notice: Subject to any disclaimer, the term of this patent is extended or adjusted under 35 U.S.C. 154(b) by 12 days.

(21) Appl. No.: 11/220,241

(22) Filed: Sep. 6, 2005

(51) Int. Cl.
*A01H 5/00* (2006.01)

(52) U.S. Cl. ..... Plt./353
(58) Field of Classification Search ..... Plt./353
See application file for complete search history.

(56) References Cited

PUBLICATIONS http://www.plantdelights.com/Catalog/Current/Detail/05980.html.*
UPOV ROM GTITM Computer Database, GTI Jouve Retrieval Software 2005/05 citation for 'High Society'.*

* cited by examiner

*Primary Examiner*—Wendy Haas
(74) *Attorney, Agent, or Firm*—Penny J. Aguirre

(57) ABSTRACT

A new cultivar of *Hosta* named 'High Society', a sport of *Hosta* 'June', that is characterized by its unique variegated foliage with wide blue-green margins comprising about two thirds of the leaf area, centers that emerge yellow green turning to white, with intermediate areas of bright green. 'High Society' is a smaller *Hosta*, in comparison to 'June', with a mounded plant habit and pinkish white flowers held above the foliage that are present from late summer to early fall.

2 Drawing Sheets

Botanical classification: *Hosta hybrida.*
Cultivar designation: 'High Society'.

BACKGROUND OF THE INVENTION

The present invention, *Hosta* 'High Society', relates to a new and distinct cultivar of *Hosta,* botanically known as a *Hosta hybrida*, hereinafter referred to as 'High Society'.

The inventor discovered the new cultivar, 'High Society', in summer of 1999 in a tissue culture lab in Waseca, Minn. 'High Society' originated as a naturally occurring sport of *Hosta* 'June' (unpatented). 'High Society' is unique in having foliage with wide intensely blue-green margins and white centers with distinct bright green areas in the region where the margins and centers meet. The parent plant 'June' differs primarily in having variegated foliage with narrower blue-green margins and yellow-green centers that do not turn white as they mature. 'High Society' is also smaller than 'June' in both height and spread.

Asexual reproduction of the new cultivar was first accomplished by the inventor utilizing *in vitro* propagation in Waseca, Minn. in fall of 2002. Asexual reproduction of the new cultivar by division and tissue culture has shown that the unique features of 'High Society' are stable and reproduced true to type in successive generations.

SUMMARY OF THE INVENTION

The following traits have been repeatedly observed in trials in Minnesota for a period of six years and represent the characteristics of the new cultivar. These attributes in combination distinguish 'High Society' as a new and unique cultivar of *Hosta.*

1. The foliage of 'High Society' is variegated with intense blue-green margins and centers that emerge yellow-green and mature to white, margin width comprises about two thirds of the leaf area. The foliage of the parent plant, 'June', has narrower blue-green margins and centers that remain yellow-green.
2. 'High Society' is a relatively small *Hosta* with a mounded plant habit, reaching a height of about 20 cm (exclusive of flower scapes) and a spread of about 45 cm in six years. smaller than the parent plant 'June'.
3. 'High Society' blooms in late summer with pinkish white flowers that arise above the foliage.

BRIEF DESCRIPTION OF THE DRAWING

The accompanying colored photographs illustrate the overall appearance and distinct characteristics of the new *Hosta.* The photographs were of mature plants of 'High Society' and 'June' as grown outdoors in Waseca, Minn. under the same conditions for six years.

Figure 1:
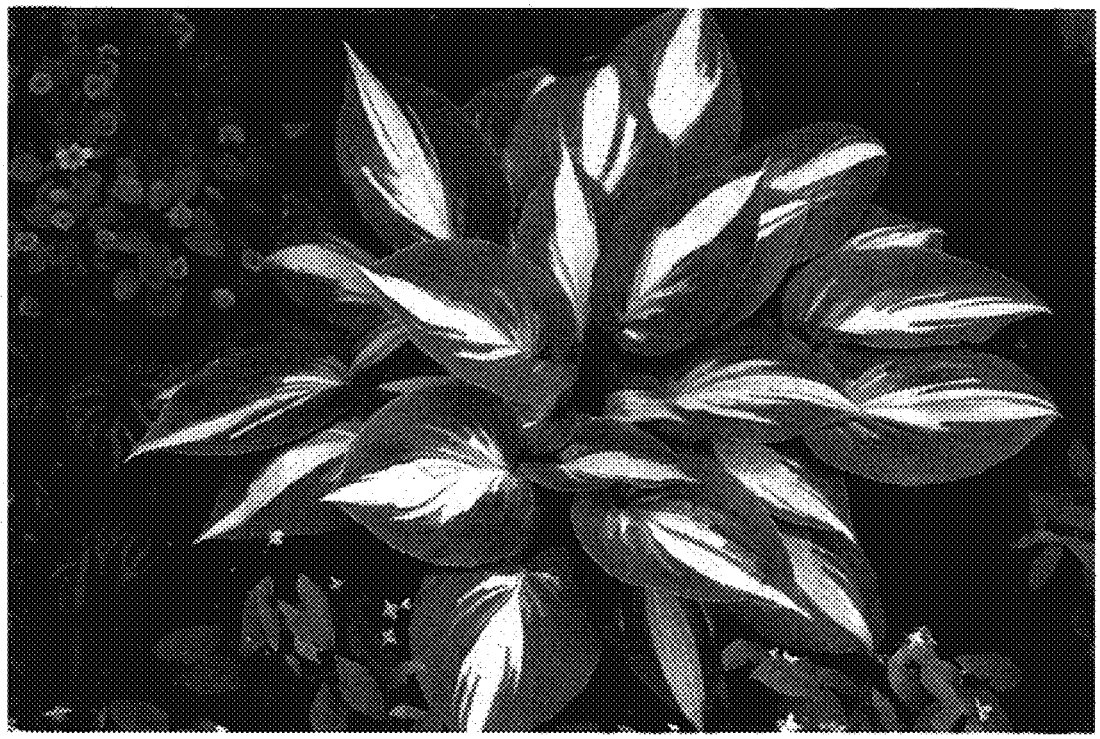
FIG. 1 was taken in June and provides an overall view of the plant habit and the spring foliage of the new cultivar, 'High Society'.
Figure 2:
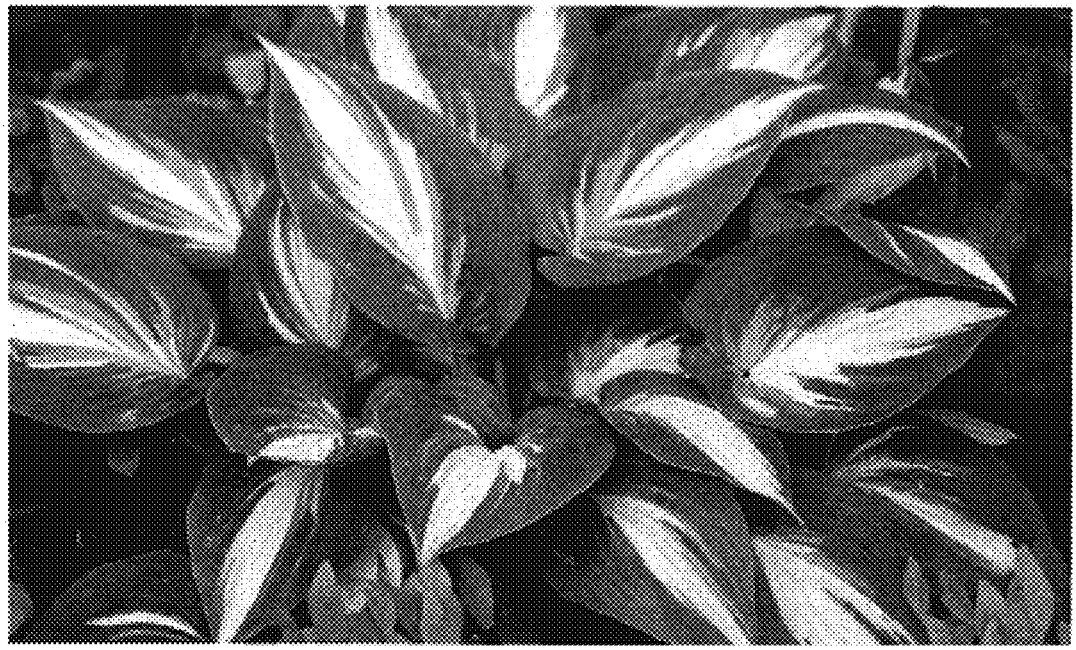
FIG. 2 was taken in August and provides a view of the summer foliage of the new cultivar.
Figure 3:
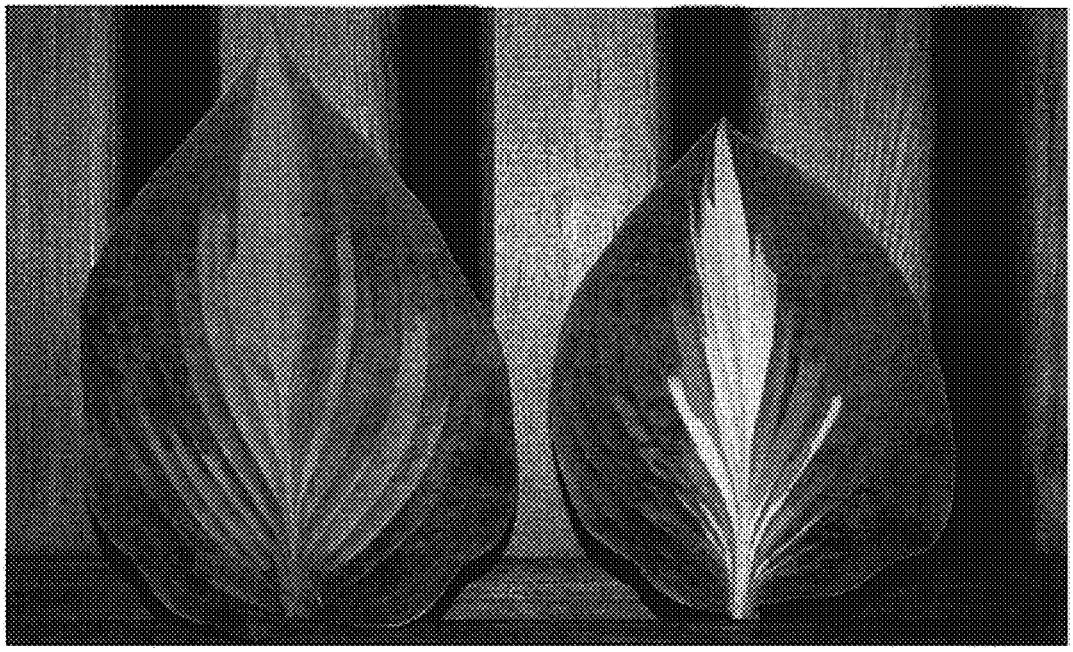

The photograph in FIG. 3 was taken in August and provides a comparison between a leaf of 'High Society' (shown on right) and 'June' (shown on left) as grown in medium shade.

The colors in the photographs are as close as possible with the photographic and printing technology utilized and combined with the color values cited in the detailed botanical description accurately describe the colors of the new *Hosta.*

DETAILED BOTANICAL DESCRIPTION OF THE PLANT

The following is a detailed description of six year-old plants of the new cultivar as grown outdoors in Waseca, Minn. The phenotype of the new cultivar may vary with variations in environmental, climatic, and cultural conditions, as it has not been tested under all possible environmental conditions. The color determination is in accordance with the 2001 R.H.S. Colour Chart of The Royal Horticultural Society, London, England, except where general color terms of ordinary dictionary significance are used.

Botanical classification: 'High Society' is a cultivar of *Hosta hybrida*.

Parentage: Naturally occurring sport of *Hosta* 'June' (not patented).

General description:

*Blooming period.*—About 4 weeks from early August to early September.

*Plant habit.*—Herbaceous perennial, clump-forming, mounded habit.

*Height and spread.*—Reaches about 20 cm (8 in) in height (excluding flower scapes) and about 45 cm (18 in) in width.

*Hardiness.*—U.S.D.A. Zones 3 to 8.

*Culture.*—Light to full shade, moist soils of moderate fertility.

*Diseases and pests.*—Above average substance confers some resistance to slugs. No susceptibility or resistance to diseases or other pests has been observed for 'High Society'.

*Root description.*—Freely branched, fleshy.

*Propagation.*—*In vitro* propagation is the preferred method utilizing typical methods for *Hosta*, division are also possible.

*Root development.*—Rooted transplants from tissue culture fully develop in a 96-cell liner in about 6 to 8 weeks in a greenhouse with average temperatures of about 70° F.

*Growth rate.*—Slow to moderate.

Foliage description:

*Leaf shape.*—Broadly ovate.

*Leaf division.*—Simple.

*Leaf base.*—Cordate.

*Leaf apex.*—Cuspidate.

*Leaf venation.*—11 pairs of veins, camptodrome pattern, impressed on upper surface and raised on lower surface, color on margin region is 191B on upper and lower surface, color in centers matches center foliage coloration.

*Leaf margins.*—Entire, flat without undulations.

*Leaf attachment.*—Petiolate.

*Leaf arrangement.*—Basal, radiate spirally from base.

*Leaf surface.*—Slightly glaucous on upper surface, glaucous on lower surface.

*Leaf substance.*—Above average.

*Leaf orientation.*—Held nearly horizontal on petioles held upright or up to about a 45° angle to center.

*Leaf variegation pattern.*—Margins comprise about two thirds of the leaf area and average about 3.8 to 4 cm in width, the centers have an oblanceolate-shaped pattern in the center (up to about 2 cm in width) with additional narrower areas radiating out from the basal region, the intermediate area exists in an irregular pattern between the boundaries of the margins and centers.

*Leaf color.*—Spring foliage, upper surface; centers emerge 150C and change to 2D, margins N138A, intermediate area (between the margins and centers) 144A, lower surface; centers emerge 154C and change to 2D, margins emerge 146A and change to 137B, intermediate areas 144A. Summer foliage, upper surface; centers 155A, margins 139A, intermediate areas 144A, lower surface; centers 155A, margins 137A, intermediate areas 144A.

*Leaf size.*—Average of 12 cm in length, average of 10 cm in width.

*Leaf quantity.*—About 5 to 7 per shoot (eye).

*Petiole size.*—About 16 cm. in length, about 1 cm. in width.

*Petiole color.*—Variegation that radiates into leaf blade, center matches leaf center coloration with stripes of intermediate area color and margin color near the edges on upper surface, lower surface 1445D with a thin stripe of 144A near edges.

*Petiole surface.*—Glabrous.

*Petiole shape.*—Sulcate.

Flower scape description:

*Scape shape.*—Round, solid.

*Scape number.*—One per mature eye under normal growing conditions.

*Scape posture.*—Straight, held upright at about 90° from horizontal.

*Scape size.*—About 25 cm in length, about 4 cm in width.

*Scape color.*—144C with specks of 70A.

*Scape surface.*—Glabrous.

*Leaf bracts.*—About 2, internodes of 3 cm, about 3 cm in length and 1.5 cm in width, ovate and cupped in shape, color of upper and lower surface is variegated with edges 144A and centers 144D blushed with 70B, glabrous in texture.

Flower description:

*Inflorescence type.*—Terminal racemes of single bell-shaped flowers.

*Lastingness of inflorescence.*—About 4 weeks from first opening bloom to fading of last opening bloom, individual blooms last about 1 day.

*Flower shape.*—Bell-shaped.

*Flower number.*—About 25 to 30 per scape.

*Flower internode length.*—Up to about 1 cm.

*Flower fragrance.*—None detected.

*Flower bud shape.*—Spathulate.

*Flower bud size.*—Up to about 3.5 cm in length and 1.2 cm in diameter.

*Flower bud color.*—76B with vertical markings of 76A.

*Flower size.*—About 5 cm in length and about 2 cm in diameter; tube region is about 1.8 cm in length and 3.5 mm in width and expanded region is about 3 cm in length and 2 cm in width.

*Flower color.*—76C with fine vertical markings of 76B.

*Pedicels.*—About 5 mm in length, 2 mm in diameter, 76A specked with N82C in color.

*Perianth features.*—Comprised of 6 tepals, 3 interior and 3 exterior, fused in tube region and lower half of expanded region, partially overlapping on upper one half of expanded region.

*Tepal shape.*—Oblanceolate.

*Tepal size.*—About 5 cm in length, about 1.2 cm in width.

*Tepal color.*—Outer and inner surface 76D, inner surface striped with 76A and blushed with 76B, outer surface striped with 76B and blushed with 76C.

*Tepal texture.*—Glabrous.

*Floral bracts.*—1 per flower, ovate in shape, glabrous surface, variegated in color with margins 144A and centers 144D with faint blush of 70B, up to about 2.5 cm in length and 1.5 cm in width.

Reproductive organs:

*Gynoecium.*—1 Pistil. Style is about 5 cm in length, 1 mm in width, 157D in color and extends about 7 mm beyond perianth. Stigma is 3-lobed and 3A in color. Ovary is superior, compound, composed of 3 locules, 5 mm in length, 2.5 mm in width and 144D in color.

*Androecium.*—6 stamens. Filament is 157D in color, 5.5 cm in length, 1 mm in width, extends about 7 mm beyond perianth. Anthers are 4 mm in length, 1.5 mm in width, attachment is versatile, 202A in color, dehiscence is longitudinal, pollen is abundant and 14B in color.

*Fruit.*—Fruit development was not observed.

I claim:

1. A new and distinct cultivar of *Hosta* plant named 'High Society' as herein illustrated and described.

* * * * *